United States Patent [19]

Schmidt et al.

[11] Patent Number: 4,777,273

[45] Date of Patent: Oct. 11, 1988

[54] PREPARATION OF ALKYL (6R,7S,8R)-6,9-DIHYDROXY-7,8-ISO-PROPYLIDENEDIOXY-2,4-NONADIENO-ATES AND THEIR USE FOR THE PREPARATION OF D-BIOTIN

[75] Inventors: Richard R. Schmidt; Martin Maier, both of Constance, Fed. Rep. of Germany

[73] Assignee: BASF Aktiengesellschaft, Rheinland-Pfalz, Fed. Rep. of Germany

[21] Appl. No.: 899,792

[22] Filed: Aug. 25, 1986

Related U.S. Application Data

[63] Continuation of Ser. No. 500,569, Jun. 2, 1983, abandoned.

[30] Foreign Application Priority Data

Jul. 1, 1982 [DE] Fed. Rep. of Germany ....... 3224511

[51] Int. Cl.$^4$ .......................................... C07D 317/30
[52] U.S. Cl. ................................................ 549/454
[58] Field of Search ......................................... 549/454

[56] References Cited

U.S. PATENT DOCUMENTS 4,450,276  5/1984  Gelhaus et al. ............. 549/454 X

FOREIGN PATENT DOCUMENTS 3122562  11/1982  Fed. Rep. of Germany ...... 549/454

OTHER PUBLICATIONS

Vogel et al. (Liebigs Ann. Chem. 1980, 1972–77).
M. Maier (cf. Degree Thesis, University of Konstanz, 1981).
Chemical Abstract 98:107081c (1983) equivalent to DE 3122562.
Chemical Abstract 98:34422c (1983).
Chemical Abstracts Band 94, Nr. 15, Apr. 13, 1981, Columbus, Ohio, USA: F. Vogel et al. "(+)-Biotin from D-arabinose", Seite 688, Spalte 2, Abstract Nr. 121 407 n & Liebigs Ann. Chem. Band 1980, Nr. 12, Seiten 1972–1977 (Kat. D).
Martin Maier, "Entwicklung Einer Kurzen und Effektiven Biotinsynthese".

Primary Examiner—Nicky Chan
Attorney, Agent, or Firm—Oblon, Fisher, Spivak, McClelland & Maier

[57] ABSTRACT

Alkyl (6R,7S,8R)-6,9-dihydroxy-7,8-isopropylidene-dioxy-2,4-nonadienoates of the formula I

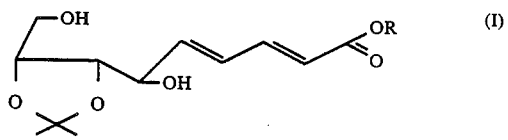

where R is alkyl of 1 to 4 carbon atoms are prepared by reacting 3,5-O-isopropylidene-D-arabinose of the formula II

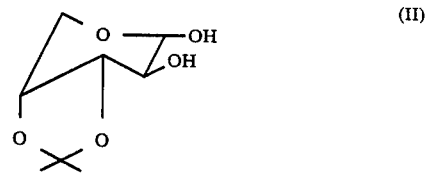

with a 3-carboalkoxyprop-2-en-1-ylidene triphenylphosphorane of the formula III

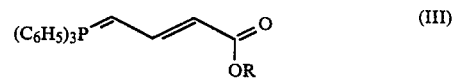

in a solvent at elevated temperatures, by a process wherein the reaction is carried out in, as the solvent, a suitable aliphatic or aromatic hydrocarbon, a halogen derivative thereof or a cycloaliphatic ether, preferably an aromatic hydrocarbon of 6 to 8 carbon atoms, at from 65 to 130° C., preferably from 80 to 115° C.

Using this process, the basic skeleton of d-biotin can be synthesized from D-arabinose in substantially better yields than obtainable hitherto.

5 Claims, No Drawings

PREPARATION OF ALKYL (6R,7S,8R)-6,9-DIHYDROXY-7,8-ISOPROPYLIDENEDIOXY-2,4-NONADIENOATES AND THEIR USE FOR THE PREPARATION OF D-BIOTIN

This application is a continuation of application Ser. No. 500,569, filed June 2, 1983 now abandoned.

The present invention relates to a process for the preparation of alkyl(6R,7S,8R)-6,9-dihydroxy-7,8-isopropylidenedioxy-2,4-nonadienoates by reacting 3,4,-O-isopropylidene-D-arabinose with 3-carbomethoxyprop-2-en-1-ylidene triphenylphosphorane, and the use of the product for the preparation of di-biotin of the formula

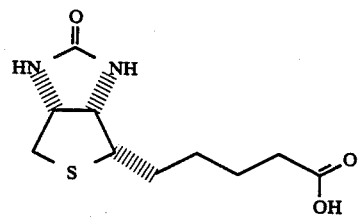

Like all vitamins, biotin has become increasingly important in the last few years. Only the d form of biotin is physiologically active, and there has hence been no lack of attempts to find an economical process for the prepartion of this form. In order to avoid the generally very expensive racemate separation, the efforts have been concentrated on preparing the desired chiral compounds by stereospecific conversion of conveniently obtainable chiral precursors. For example, Japanese authors have published biotin syntheses in which the basic skeleton of this vitamin is built up from naturally occurring hexoses (cf. for example, H. Ohrui et al., Tetrahedron Lett. 1975, 2765). The disadvantage of this comparatively economical process is that it is necessary to shorten the initial carbon skeleton by 1 carbon atom.

Attempts have therefore been made to use a readily obtainable pentose, in particular D-arabinose, as a starting material.

If it is desired to prepare d-biotin from D-arabinose, it is necessary to link a $C_4$ chain to the 1-position, form a thiophane ring between positions 2 and 5, and introduce N atoms after the 3- and 4-positions. The N atoms are advantageously introduced at the end of the synthesis route, and the 3- and 4-positions are therefore protected at the beginning.

For example, F. Vogel et al. (cf. Liebigs Ann. Chem. 1980, 1972-77) have tried to prepare methyl(6R,7S,8R)-6,9-dihydroxy-7,8-isopropylidenedioxy-2,4-nonadienoate of the formula Ia

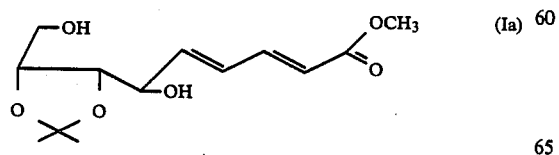

by reacting the 3,4-isopropylidene derivative of the formula II

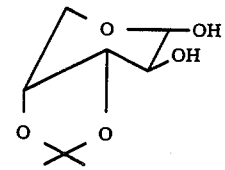

which is readily obtainable from arabinose, with 3-carbomethoxyprop-2-en-1-ylidene triphenylphosphorane of the formula IIIa

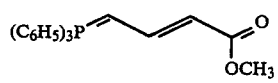

The product of this reaction could be catalytically hydrogenated to the corresponding saturated compound, which in turn could be converted to d-biotin in 8 stages by the process of Ohrui et al. (cf. Tetrahedron Lett. (1975), 3657). However, according to the authors, the results of these experiments were not very encouraging. Although they obtained complete conversion with II benzylated in the 2-position, the resulting reaction mixture was very complex. Even where II benzoylated in the 2-position was employed, the reaction to lengthen the chain at the 1-position of arabinose gave a yield of only about 13%.

As part of his degree thesis, M. Maier (cf. Degree Thesis, University of Konstanz, 1981) carried out a further investigation into the reaction of II with III.

He carried out the reaction in dimethylformamide/$CH_2Cl_2$ (1:1), dimethylsulfoxide and dimethoxyethane at 85° and 90° C. in the presence of catalytic amounts of benzoic acid, and obtained yields of I of from 33 to 39% of theory. On page 19, lines 1–2, of his degree thesis, he writes the following about this reaction: "Even when the reaction conditions were varied, it was not possible to improve the yields substantially". However, yields of this order of magnitude are not sufficient for an industrial process.

It is an object of the present invention to provide a process by means of which D-arabinose, which is readily available, can be converted to the biotin intermediate I in a simple manner and in good yields.

We have found that this object is achieved, and that, surprisingly, I can be obtained in very good yields by reacting II with III, if the reaction is carried out in, as the solvent, a suitable aliphatic or aromatic hydrocarbon, a halogen derivative thereof or a cycloaliphatic ether, at from 80° to 115° C.

The present invention accordingly relates to a process for the preparation of alkyl(6R,7S,8R)-6,9-dihydroxy-7,8-isopropylidenedioxy-2,4-nonadienoates of the general formula I

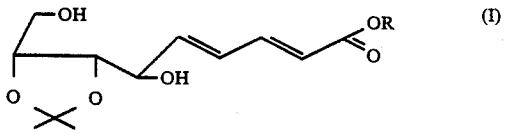

where R is alkyl of 1 to 4 carbon atoms, preferably methyl, by reacting 3,4-O-isopropylidene-D-arabinose of the formula II

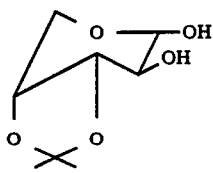

(II)

with a 3-carboalkoxyprop-2-en-1-ylidene triphenylphosphorane of the formula III

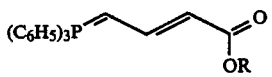

(III)

in a solvent at elevated temperatures, wherein the reaction is carried out in, as the solvent, a suitable aliphatic or aromatic hydrocarbon, a halogen derivative thereof or a cycloaliphatic ether, preferably an aromatic hydracarbon of 6 to 8 carbon atoms, in particular toluene, at from 65° to 130° C., preferably from 80° to 115° C.

It was very surprising that in the reaction of II with III, under the conditions according to the invention, the formation of undesirable by-products, in particular of cyclic compounds by an intramolecular Michael addition reaction of the free hydroxyl groups with the $\alpha,\beta,\gamma,\delta$-unsaturated system, as observed to a great extent by Vogel et al. (loc. cit.) in the reaction of II benzoylated in the 2-position, was substantially suppressed in spite of the fact that in the D-arabinose used the hydroxyl groups in the 1- and 2-positions were unprotected. As a result, the compounds of the formula I required for the preparation of d-biotin were obtained in yields which are extremely good considering the high reactivity of the reactants employed.

The 3,4-O-isopropylidene-D-arabinose II required as a starting compound can be obtained, in a yield of about 83%, by a kinetically controlled reaction with isopropenyl ether or 2,2-dimethoxypropane in the presence of a catalytic amount of p-toluenesulfonic acid (cf. J. Gelas and D. Horton, Carbohydr. Res. 45 (1975), 181; and M. Kiso and A. Hasegawa, Carbohydr. Res. 52 (1976), 95).

The ylide III can be obtained by reacting an alkyl $\gamma$-bromocrotonate with triphenylphosphine in toluene, and reacting the resulting phosphonium salt with NaOH.

Suitable non-polar aprotic solvents, ie. those having a low dielectric constant ($\epsilon < 15$) and a small dipole moment ($\mu = 0-2$ Debye), can be employed.

These essentially include aliphatic and aromatic hydrocarbons which are suitable as solvents, and halogen derivatives of these. Advantageously, the solvent used is one (a) in which the compounds participating in the novel reaction are readily soluble and (b) which has a boiling point which permits the reaction to be carried out at from 80° to 120° C. under atmospheric pressure. Accordingly, particularly suitable solvents are aromatic hydrocarbons of 6 to 8 carbon atoms, eg. benzene, toluene or xylene, in particular toluene.

Examples of suitable halohydrocarbons are chlorobenzene and 1,2-dichloroethane.

However, a cycloaliphatic ether, eg. tetrahydrofuran or 1,4-dioxane, can also be advantageously used as the solvent. Cycloaliphatic ethers cannot be regarded as being direct members of the group comprising the nonpolar aprotic solvents, but they, too, possess a low dielectric constant ($\epsilon < 15$) and a small dipole moment ($\mu = 0-2.5$ Debye).

Investigation of the reaction mixtures by thinlayer chromatography shows that the reaction in a cycloaliphatic ether gives a somewhat greater amount of by-products than that in a hydrocarbon.

To carry out the process, in general 3,4-O-isopropylidene-D-arabinose which has been finely powdered, and dried under greatly reduced pressure, is dissolved in the solvent at room temperature, 3-carboalkoxyprop-2-en-1-ylidene triphenylphosphorane is added to the solution under a protective gas atmosphere, and the mixture is heated, under this atmosphere and in the absence of moisture, in a reaction vessel provided with a reflux condenser.

The progress of the reaction can be monitored by examining small samples by thin-layer chromatography. This was carried out in general over silica gel, using pure ethyl acetate as the mobile phase.

The reaction mixture is worked up in a conventional manner by cooling, evaporating down the solution under reduced pressure, taking up the residue in ethyl acetate, filtering off the solution from precipitated phosphine oxide and purifying the resulting extract by chromatography over silica gel. Where a relatively pure extract is obtained, as is the case, for example, when toluene is used, it is sufficient to remove the excess of Wittig reagent present in the extract by means of a short silica gel column.

The novel reaction gives very good yields of, for example, methyl(6R,7S,8R)-6,9-dihydroxy-7,8-isopropylidenedioxy-2,4-nonadienoate in the form of an EE/EZ isomer mixture in which the EE isomer predominates. Catalytic hydrogenation of this product gives a virtually quantitative yield of methyl(6R,7S,8R)-6,9-dihydroxy-7,8-isopropylidene-dioxy-2,4-nonanoate, which in turn can be converted to d-biotin, for example by the process of Ohrui (cf. Tetrahedron Lett. 1975, 3657), in 8 simple stages. Thus, the novel route for synthesizing d-biotin from D-arabinose requires only 11 stages and gives substantially better yields than those obtainable hitherto.

This route requires fewer reaction steps than other syntheses of d-biotin from carbohydrates. For example, Ohrui et al. require 16 reaction steps in their process employing D-mannose or D-glucosamine (cf. Tetrahedron Lett. 1975, 3657 or Agr. Biol. Chem. 42 (1978), 865), Vogel et al. require 15 reaction steps in their process employing D-arabinose (cf. Liebigs Ann. Chem. 1980, 1972) and Ogawa et al. require 22 steps in their process employing D-glucose (cf. Carbohydr. Res. 57 (1977), C31).

EXAMPLE 1

Preparation of methyl(6R,7S,8R)-6,9-dihydroxy-7,8-isopropylidene-dioxy-2,4-nonadienoate in boiling toluene 1.0 g (5.26 millimoles) of 3,4-O-isopropylidene-D-arabinose, finely powdered, and dried under greatly reduced pressure, was dissolved in 150 ml of absolute toluene at room temperature, the apparatus was filled with dry nitrogen and 2.08 g (5.78 millimoles) of [3-carbomethoxyprop-2-en-1-ylidene]-triphenylphosphorane were added, the latter being brought into suspension by rotating the reaction vessel. The reaction mixture was then heated, and refluxed under a slow stream of nitrogen, the relux condenser being equipped with an NaOH tube. After 15 minutes, it was no longer possible to detect the starting sugar by means of thin-layer chromatography (mobile phase: pure ethyl acetate). After boiling for 30 minutes, the mixture was cooled to 20° C., and the dark solution was evaporated down under reduced pressure to give 3.22 g of a reddish brown oil. This residue was taken up in about 5 ml of ethyl acetate, and the solution was chromatographed over a short silica gel column (diameter 6.5 cm, length 4.5 cm) using ethyl acetate. After a first fraction of 100 ml was obtained, the subsequent 130 ml contained chromatographically pure methyl(6R,7S,8R)-6,9-dihydroxy-7,8-isopropylidenedioxy-2,4-nonadienoate in the form of an EE/EZ mixture (predominantly EE). Yield: 1.17 g (82% of theory).

EXAMPLE 2

Preparation of methyl(6R,7S,8R)-6,9-dihydroxy-7,8-isopropylidenedioxy-2,4-nonadienoate in tetrahydrofuran 1.0 g (5.26 millimoles) of 3,4-O-isopropylidene-D-arabinose, finely powdered, and dried under greatly reduced pressure, was dissolved in 100 ml of absolute tetrahydrofuran at room temperature, the apparatus was filled with dry nitrogen and 2.42 g (6.71 millimoles) of [3-carbomethoxyprop-2-en-1-ylidene]-triphenylphosphorane were added. The dark yellow solution was then refluxed for a total of 5 hours under a slow stream of dry nitrogen (after 4 hours, the starting sugar was no longer detectable by thin-layer chromatography). The reaction mixture was evaporated down under reduced pressure to give 3.78 g of a dark yellow resin. This residue was taken up in 5 ml of ethyl acetate, and the solution was chromatographed over a silica gel column (diameter 6.5 cm, length 3.5 cm) using ethyl acetate as the mobile phase. After a first fraction of 100 ml was obtained, the principal fraction of 300 ml gave 3.39 g of solid product, which was once again dissolved in 5 ml of ethyl acetate, and chromatographed over a silica gel column (diameter 5 cm, length 16 cm) using pure ethyl acetate. In this manner, 1.01 g (71% of theory) of chromatographically pure methyl(6R,7S,8R)-6,9-dihydroxy-7,8-isopropylidenedioxy-2,4-nonadienoate were obtained as an EE/EZ isomer mixture. In addition, a subsequent fraction of 0.11 g, comprising about equal amounts of the desired product and triphenylphosphine, was obtained.

EXAMPLES 3 TO 6 AND COMPARATIVE EXAMPLES

In each case, 1.0 g of 3,4-O-isopropylidene-D-arabinose was reacted with 2.08 g of 3-carbomethoxyprop-2-en-1-ylidene triphenylphosphorane in a solvent, using a procedure similar to that described in Example 1. The solvents used, the amounts of these, the reaction temperatures, the reaction times and the yields of methyl(6R,7S,8R)-6,9-dihydroxy-7,8-isopropylidenedioxy-2,4-nonadienoate achieved are summarized in Tables 1 and 2.

TABLE 1

| Example | Solvent | Temperature [°C.] | Time [min] | Yield [%] |
|---|---|---|---|---|
| 3 | Toluene (140 ml) | 80 | 30 | 76 |
| 4 | Benzene (150 ml) | Boiling (80) | 30 | 67 |
| 5 | 1,4-Dioxane (120 ml) | Boiling (102) | 40 | 77 |
| 6 | 1,2-Dichloroethane (120 ml) | Boiling (84) | 30 | 68 |

TABLE 2

| Comparative Examples | Solvent | Temperature [°C.] | Time [min] | Yield [%] |
|---|---|---|---|---|
| 7 | Acetonitrile | Boiling (82.6) | 30 | + |
| 8 | Ethanol | Boiling (79) | 20 | 25++ |
| 9 | Ethanol+++ | Boiling | 20 | 35++ |

+Thin-layer chromatography showed that the mixture was very complex, and hence it was not worked up
++Pronounced signs of decomposition
+++Carried out in the presence of 60 mg of benzoic acid

We claim:

1. A process for the preparation of an alkyl(6R,7S,8R)-6,9-dihydroxy-7,8-isopropylidenedioxy-2,4-nonadienoate of formula I

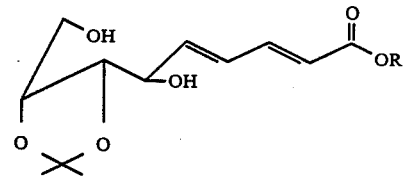

wherein R is a $C_{1-4}$ alkyl group comprising reacting a 3,4-O-isopropylidene-D-arabinose of formula II

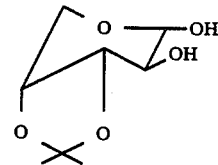

with a phosphorylide of formula III

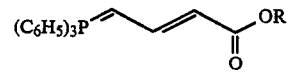

in a $C_{6-8}$ aromatic hydrocarbon solvent at a temperature of from 80°–115° C.

2. The process of claim 1, wherein said process is run under a protective gas atmosphere and in the absence of moisture.

3. The process of claim 1, wherein R is methyl.

4. The process of claim 1, wherein the said solvent is benzene, toluene or xylene.

5. The process of claim 1, wherein the said reaction is carried out in boiling toluene.

* * * * *